United States Patent [19]
Gallenkamp et al.

[11] Patent Number: 6,160,121
[45] Date of Patent: Dec. 12, 2000

[54] PYRIDYL-THIAZOLES AND THEIR USE TO PROTECT PLANTS AGAINST INFECTIONS BY MICRO-ORGANISMS

[75] Inventors: Bernd Gallenkamp, Wuppertal; Klaus Stenzel, Düsseldorf; Gerd Hänssler, Leverkusen; Stefan Dutzmann, Langenfeld; Heinz-Wilhelm Dehne, Bonn, all of Germany

[73] Assignee: Bayer Aktiengesellschaft, Leverkusen, Germany

[21] Appl. No.: 09/317,318

[22] Filed: May 24, 1999

Related U.S. Application Data

[62] Division of application No. 08/952,353, filed as application No. PCT/EP96/02052, May 14, 1996, Pat. No. 5,945,380.

[51] Int. Cl.⁷ .................................................. C07D 213/50
[52] U.S. Cl. ............................................................ 546/314
[58] Field of Search ............................................. 546/314

[56] References Cited

U.S. PATENT DOCUMENTS 5,149,822   9/1992   Lindel et al. ........................... 546/315

FOREIGN PATENT DOCUMENTS

| 169502 | 1/1986 | European Pat. Off. . |
| 268775 | 6/1988 | European Pat. Off. . |
| 93/10095 | 5/1993 | WIPO . |

OTHER PUBLICATIONS

CA 117:131190, Pilkington, 1992.
CA 87:135172, Le Count et al., 1977.
CA 99:171328, Ishihara Sangyo Kaisha, Ltd, 1983.
CA 115:207929, Broom et al., 1991.
CA 116:230208, Haga et al., 1992.

*Primary Examiner*—Jane Fan
*Attorney, Agent, or Firm*—Norris, McLaughlin & Marcus, P.A.

[57] ABSTRACT

Pyridyl-thiazoles of the formula

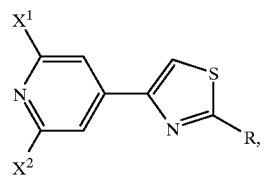

(I)

intermediates of the formulae

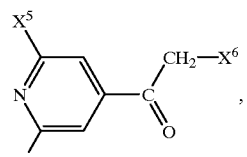

(IIa)

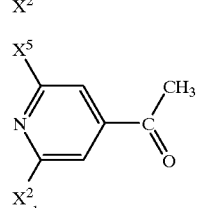

(X)

and

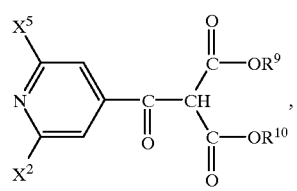

(XI)

and their salts and acid adducts suitable for the protection of plants against attack by undesirable microorganisms are disclosed.

2 Claims, No Drawings

PYRIDYL-THIAZOLES AND THEIR USE TO PROTECT PLANTS AGAINST INFECTIONS BY MICRO-ORGANISMS

This appln is a Div of Ser. No. 08/952,353 Nov. 19, 1997 now U.S. Pat. No. 5,945,380, Aug. 31, 1998 which is a 371 of PCT/EP96/02052 May 14, 1996.

The present invention relates to new pyridyl-thiazoles, several processes for their preparation and their use for protecting plants against attack by undesirable microorganisms.

It has already been disclosed that certain hatogenopyridine-4-carboxylic acid derivatives can be employed for generating resistance in plants against attack by phytopathogenic microorganisms (cf. EP-OS (European Published Specification) 0 268 775 and DE-OS (German Published Specification) 4 138 026). Thus, for example, 2,6-dichloropyridine-4-carboxylic acid, methyl 2,6-dichloropyridine-4-carboxylate and α-(4-chlorophenyl)-benzyl 2,6-dichloropyridine-4-carboxylate can be used for the purpose mentioned. However, the action of these substances is not always satisfactory, above all when low amounts are applied. Furthermore, the direct fungicidal action of these compounds leaves something to be desired.

New pyridyl-thiazoles of the formula

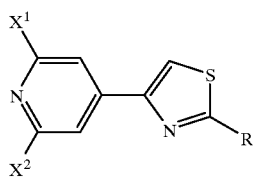
(I)

in which
  R represents alkyl,

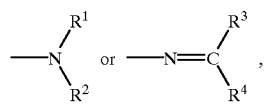

wherein
  $R^1$ represents hydrogen or —CO—$R^5$,
  $R^2$ represents hydrogen or —CO—$R^6$,
  $R^3$ represents hydrogen or alkyl,
  $R^4$ represents alkoxy or dialkylamino,
  $R^5$ and $R^6$ independently of one another represent alkyl, alkoxycarbonyl, alkylamino, optionally substituted aryl, optionally substituted arylamino or optionally substituted arylsulphonylamino, or
  $R^1$ and $R^2$, together with the nitrogen atom to which they are bonded, represent a cyclic imide of the formula

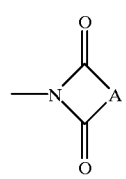

wherein
  A represents optionally substituted alkanediyl or optionally substituted alkenediyl, $X^1$ represents hydrogen or halogen and
$X^2$ represents halogen, and salts and acid adducts thereof have now been found.

It has furthermore been found that pyridyl-thiazoles of the formula (I) and salts and acid adducts thereof are obtained by a process in which a) halogenoacetyl-pyridines of the formula

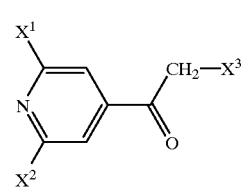
(II)

in which
  $X^1$ and $X^2$ have the abovementioned meanings and
  $X^3$ represents halogen, are reacted with thio compounds of the formula

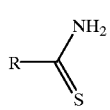
(III)

in which
  R has the abovementioned meaning, if appropriate in the presence of a diluent and if appropriate in the presence of an acid-binding agent.

or b) aminothiazoles of the formula

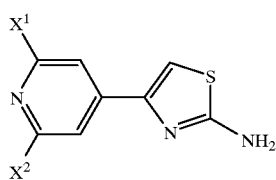
(Ia)

in which
  $X^1$ and $X^2$ have the abovementioned meanings,
  are reacted either
  α) with carboxylic anhydrides of the formulae

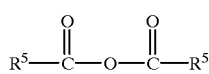
(IV)

in which
  $R^5$ has the abovementioned meaning or

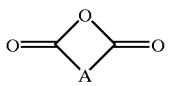
(V)

in which
A has the abovementioned meaning,
or
β) with carboxylic halides of the formula

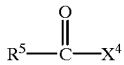
(VI)

in which
$R^5$ has the abovementioned meaning and
$X^4$ represents halogen,
or
γ) with isocyanates of the formula

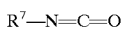 (VII)

in which
$R^7$ represents alkyl, optionally substituted aryl or optionally substituted arylsulphonyl,
or
δ) with acetals of the formula

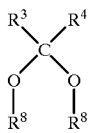
(VIII)

in which
$R^3$ and $R^4$ have the abovementioned meanings and
$R^8$ represents alkyl,
if appropriate in the presence of a diluent, if appropriate in the presence of a catalyst and if appropriate in the presence of an acid-binding agent,
and, if appropriate, the compounds of the formula (I) thus obtained are then reacted with an acid or base.

Finally, it has been found that the pyridyl-thiazoles of the formula (I) and salts and acid adducts thereof can be used particularly suitably for protecting plants against attack by undesirable microorganisms. The substances according to the invention are suitable both for generating resistance in plants against attack by undesirable microorganisms and as microbicides for combating the microorganisms directly.

Surprisingly, the substances according to the invention are more suitable for generating resistance in plants against attack by phytopathogenic microorganisms than 2,6-dichloro-pyridine-4-carboxylic acid, methyl 2,6-dichloro-pyridine-4-carboxylate and α-(4-chlorophenyl)-benzyl 2,6-dichloro-pyridine-4-carboxylate, which are structurally similar compounds which are already known from the prior art and have the same type of action. Furthermore, the substances according to the invention surprisingly are also superior in respect of their fungicidal activity to the substances already described which are structurally the most similar.

Where appropriate, the substances according to the invention can be in the form of mixtures of various possible isomeric forms, such as, for example, in the form of stereoisomers or tautomers. The invention relates both to stereoisomers and to tautomers, and also to any desired mixtures of these isomers.

Formula (I) provides a general definition of the pyridyl-thiazoles according to the invention.

R preferably represents straight-chain or branched alkyl having 1 to 6 carbon atoms or the groups

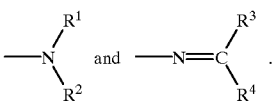

$R^1$ also preferably represents hydrogen or —CO—$R^5$.

$R^1$ also preferably represents hydrogen or —CO—$R^6$.

$R^3$ preferably represents hydrogen or straight-chain or branched alkyl having 1 to 4 carbon atoms.

$R^4$ represents alkoxy having 1 to 4 carbon atoms, or represents dialkylamino having 1 to 4 carbon atoms in each alkyl group.

$R^5$ and $R^6$ independently of one another preferably represent straight-chain or branched alkyl having 1 to 6 carbon atoms, alkoxycarbonyl having 1 to 4 carbon atoms in the alkoxy group, alkylamino having 1 to 6 carbon atoms, aryl having 6 to 10 carbon atoms, arylamino having 6 to 10 carbon atoms or arylsulphonylamino having 6 to 10 carbon atoms, it being possible for each of the three latter radicals to be mono- to trisubstituted in the aryl part in an identical or different manner by halogen, cyano, nitro, formyl, carboxyl, carbamoyl, alkyl having 1 to 6 carbon atoms, alkoxy having 1 to 6 carbon atoms, alkylthio having 1 to 6 carbon atoms, alkylsulphinyl having 1 to 4 carbon atoms, alkylsulphonyl having 1 to 4 carbon atoms, halogenoalkyl having 1 to 4 carbon atoms and 1 to 5 fluorine, chlorine and/or bromine atoms, halogenoalkoxy having 1 to 4 carbon atoms and 1 to 5 fluorine, chlorine and/or bromine atoms, halogenoalkylthio having 1 to 4 carbon atoms and 1 to 5 fluorine, chlorine and/or bromine atoms, halogenoalkylsulphinyl having 1 to 4 carbon atoms and 1 to 5 fluorine, chlorine and/or bromine atoms, halogenoalkylsulphonyl having 1 to 4 carbon atoms and 1 to 5 fluorine, chlorine and/or bromine atoms, alkoxycarbonyl having 1 to 4 carbon atoms in the alkoxy part, hydroximinoalkyl having 1 to 4 carbon atoms in the alkyl part, alkoximinoalkyl having 1 to 4 carbon atoms in the alkoxy part and 1 to 4 carbon atoms in the alkyl part and/or divalent alkanediyl having 3 or 4 carbon atoms, in which one or two (non-adjacent) carbon atoms can be replaced by oxygen and in which the alkanediyl part can be mono- to tetrasubstituted in an identical or different manner by halogen, alkyl having 1 to 4 carbon atoms and/or halogenoalkyl having 1 or 2 carbon atoms and 1 to 3 fluorine, chlorine and/or bromine atoms.

$R^1$ and $R^2$ furthermore, together with the nitrogen atom to which they are bonded, represent a cyclic imide of the formula

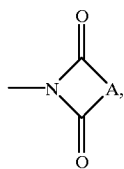

wherein

A preferably represents alkanediyl having 2 or 3 carbon atoms or alkenediyl having 2 or 3 carbon atoms, it being possible for the radicals mentioned in each case to be mono- to tetrasubstituted in an identical or different manner by halogen, alkyl having 1 to 4 carbon atoms, alkoxy having 1 to 4 carbon atoms, halogenoalkyl having 1 to 4 carbon atoms and 1 to 5 fluorine, chlorine and/or bromine atoms and/or halogenoalkoxy having 1 to 4 carbon atoms and 1 to 5 fluorine, chlorine and/or bromine atoms.

$X^1$ preferably represents hydrogen, fluorine, chlorine or bromine.

$X^2$ preferably represents fluorine, chlorine or bromine.

R particularly preferably represents methyl, ethyl, n-propyl, isopropyl, n-butyl, sec-butyl, iso-butyl, tert-butyl or the groups

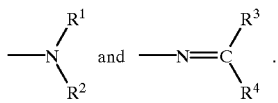

$R^1$ also particularly preferably represents hydrogen or —CO—$R^5$.

$R^2$ also particularly preferably represents hydrogen or —CO—$R^6$.

$R^3$ particularly preferably represents hydrogen, methyl or ethyl.

$R^4$ particularly preferably represents methoxy, ethoxy, dimethylamino or diethylamino.

$R^5$ and $R^6$ independently of one another particularly preferably represent methyl, ethyl n-propyl, isopropyl, n-butyl, sec-butyl, iso-butyl, tert-butyl, methoxycarbonyl, ethoxycarbonyl, methylamino, ethylamino, n-propylamino, isopropylamino, n-butylamino, sec-butylamino, iso-butylamino, tert-butylamino, phenyl, naphthyl, phenylamino, naphthylamino, phenylsulphonylamino or naphthylsulphonylamino, it being possible for each of the six latter radicals to be mono- to trisubstituted in the aryl part in an identical or different manner by fluorine, chlorine, bromine, cyano, nitro, formyl, carboxyl, carbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methoxycarbonyl, hydroximinomethyl, hydroximinoethyl, methoximinomethyl, ethoximinomethyl, methoximinoethyl or ethoximinoethyl and/or by in each case divalent trimethylene (propane-1,3-diyl), methylenedioxy or ethylenedioxy, in each case optionally mono- to tetrasubstituted in an identical or different manner by fluorine, chlorine, methyl, trifluoromethyl, ethyl or n- or i-propyl.

$R^1$ and $R^2$ furthermore, together with the nitrogen atom to which they are bonded, represent a cyclic imide of the formula

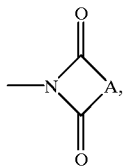

wherein

A particularly preferably represents alkanediyl having 2 or 3 carbon atoms or alkenediyl having 2 or 3 carbon atoms, it being possible for the radicals mentioned in each case to be mono- to trisubstituted in an identical or different manner by fluorine, chlorine, bromine, cyano, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy and/or trifluoroethoxy.

$X^1$ particularly preferably represents hydrogen, fluorine or chlorine.

$X^2$ particularly preferably represents fluorine or chlorine.

The definitions of radicals mentioned generally above or mentioned in the preferred ranges apply both to the end products of the formula (I) and accordingly to the particular starting substances or intermediate products required for the preparation.

These definitions of radicals can be combined with one another as desired, that is to say also between the stated ranges of preferred compounds.

Preferred compounds according to the invention are also salts which are obtainable by reaction of pyridyl-thiazoles of the formula (Ib)

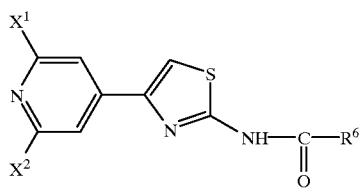

in which $R^6$, $X^1$ and $X^2$ have the abovementioned meanings, with strong bases of the formula HOMe     (IX)

in which

Me represents an alkali metal ion, one equivalent of an alkaline earth metal ion, an ammonium ion, an alkylammonium ion having 1 to 4 carbon atoms, a dialkylammonium ion having 1 to 4 carbon atoms in each alkyl group or a trialkylammonium ion having 1 to 4 carbon atoms in each alkyl group.

Particularly preferred such salts of pyridyl-thiazoles of the formula (Ib) are those in which $R^6$, $X^1$ and $X^2$ have the meanings given above as particularly preferred and Me represents a lithium, sodium or potassium ion, or represents one equivalent of a magnesium, calcium, strontium or barium ion, or represents an ammonium, methylammonium, ethylammonium, dimethylammonium, diethyl-ammonium, trimethylammonium or triethylammonium ion.

Preferred substances according to the invention are also addition products of acids and those pyridyl-thiazoles of the formula (I) in which $X^1$, $X^2$ and R have the meanings given above as preferred.

The acids which can be added on include, preferably, hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid or camphorsulphonic acid, saccharin and thiosaccharin.

If 4-bromoacetyl-2,6-dichloro-pyridine and thiourea are used as starting substances, the course of process (a) according to the invention can be illustrated by the following equation:

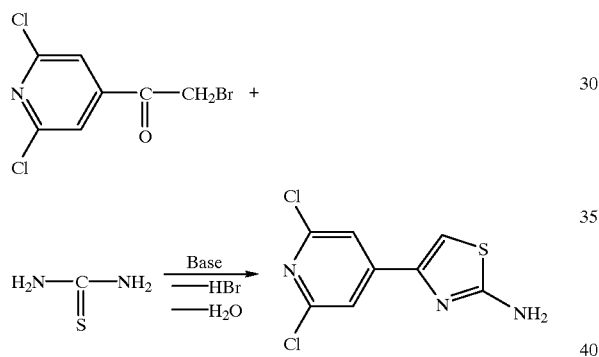

If [4-(2,6-dichloro-pyridin-4-yl)-thiazol-2-yl]-amine and acetic anhydride are used as starting substances, the course of process b), variant (α) according to the invention can be illustrated by the following equation:

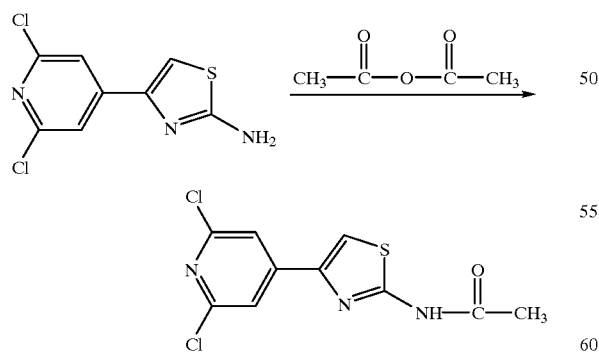

If [4-(2,6-dichloro-pyridin-4-yl)-thiazol-2-yl]-amine and 2-trifluoromethyl-phenylsulphonyl isocyanate are used as starting substances, the course of process (b), variant (γ) according to the invention can be illustrated by the following equation:

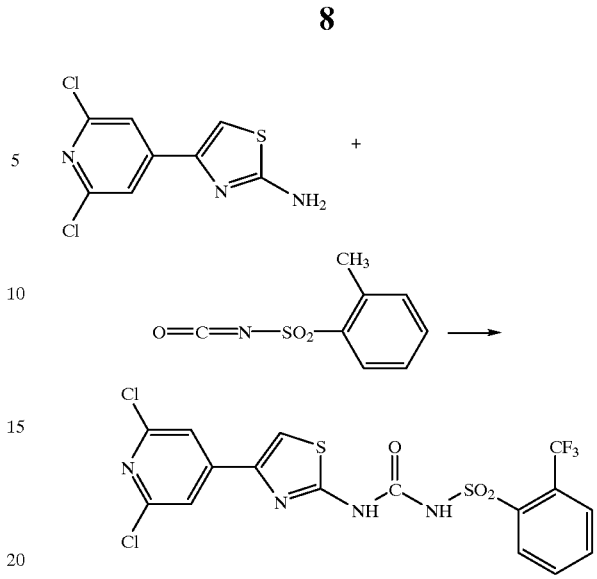

If N-[4-(2,6-dichloro-pyridin-4-yl)-thiazol-2-yl]-N'-(2-trifluoromethyl-phenylsulphonyl)-urea is used as the starting substance and sodium hydroxide is used as the reaction component, the preparation of salts by the process according to the invention can be illustrated by the following equation:

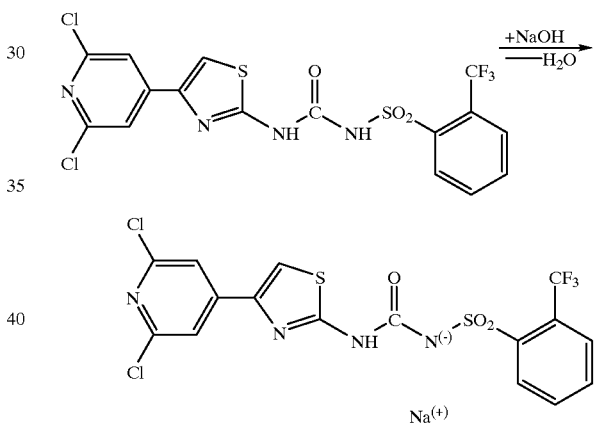

The abovementioned salt can also exist in the tautomeric form having the structure

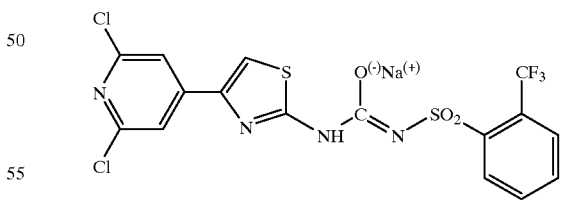

Formula (II) provides a general definition of the halogenoacetylpyridines required as starting substances for carrying out process (a) according to the invention. In this formula (II) $X^1$ and $X^2$ preferably have those meanings which have already been mentioned as preferred for $X^1$ and $X^2$ in connection with the description of the compounds of the formula (I) according to the invention. $X^3$ preferably represents chlorine or bromine.

Some of the halogenoacetl-pyridines of the formula (II) are known (cf. DE-A 1 811 833).

The halogenoacetyl-pyridines of the formula

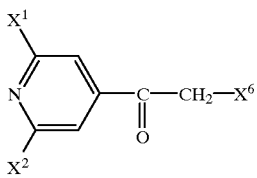
(IIa)

in which

X² represents halogen,

X⁵ represents halogen and

X⁶ represents chlorine, bromine or iodine, are new.

Formula (IIa) provides a general definition of the new halogenoacetyl-pyridines.

X² preferably represents fluorine, chlorine or bromine.

X⁵ preferably represents fluorine, chlorine or bromine.

X⁶ preferably represents chlorine or bromine.

Particularly preferred halogenoacetyl-pyridines of the formula (IIa) are those in which X² represents fluorine or chlorine, X⁵ represents fluorine or chlorine and X⁶ represents chlorine or bromine.

The new halogenoacetyl-pyridines of the formula (IIa) can be prepared by c) reacting acetylpyridines of the formula

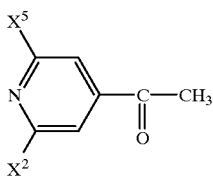
(X)

in which

X² and X⁵ have the abovementioned meanings, with halogenating agents, if appropriate in the presence of a diluent and if appropriate in the presence of a catalyst.

The known halogenoacetyl-pyridines of the formula (II) can be prepared in an analogous manner.

If 4-acetyl-2,6-dichloro-pyridine is used as the starting substance and bromine is used as the halogenating agent, the course of process (c) can be illustrated by the following equation.

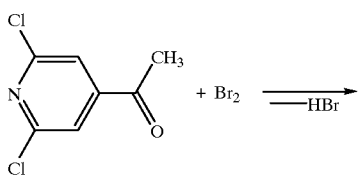

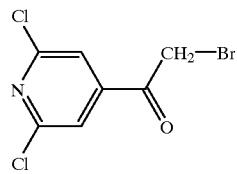

Formula (X) provides a general definition of the acetylpyridines required as starting substances in carrying out process (c). In this formula X² and X⁵ preferably have those meanings which have already been mentioned as preferred for these radicals in connection with the description of the compounds of the formula (IIa).

The acetylpyridines of the formula (X) were hitherto still unknown. They can be prepared by d) reacting malonic ester derivatives of the formula

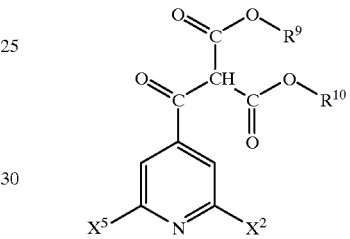
(XI)

in which

X² and X⁵ have the abovementioned meanings,

R⁹ represents alkyl and

R¹⁰ represents alkyl, with water, if appropriate in the presence of a diluent.

If dimethyl 2,6-dichloro-iso-nicotinoyl-malonate is used as the starting substance and water is used as the reaction component, the course of process (d) can be illustrated by the following equation.

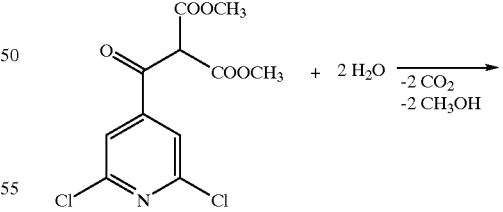

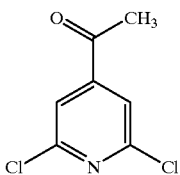

In a special variant, process (d) can also be carried out by only effecting a partial hydrolysis and decarboxylation. The esters resulting in this way of the formula

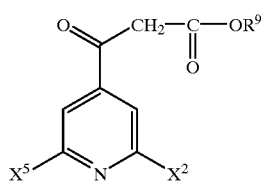

(XII)

in which
$X^2$, $X^5$ and $R^9$ have the abovementioned meanings,
can be isolated and then reacted in a further stage under the reaction conditions of process (d) to give acetylpyridines of the formula (X).

Formula (XI) provides a general definition of the malonic esters required as starting substances in carrying out process (d). In this formula $X^2$ and $X^5$ preferably have those meanings which have already been mentioned as preferred for these radicals in connection with the description of the compounds of the formula (IIa). $R^9$ preferably represents alkyl having 1 to 6 carbon atoms, particularly preferably methyl, ethyl, n-propyl, isopropyl, n-butyl, iso-butyl, sec-butyl or tert-butyl. $R^{10}$ likewise preferably represents alkyl having 1 to 6 carbon atoms, particularly preferably methyl, ethyl, n-propyl, isopropyl, n-butyl, iso-butyl, sec-butyl or tert-butyl.

The malonic ester derivatives of the formula (XI) were hitherto still unknown. They can be prepared by e) reacting isonicotinoyl halides of the formula

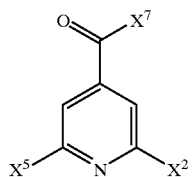

(XIII)

in which
$X^2$ and $X^5$ have the abovementioned meanings and
$X^7$ represents halogen,
with malonic esters of the formula

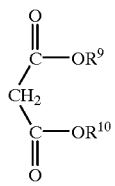

(XIV)

in which
$R^9$ and $R^{10}$ have the abovementioned meanings,
if appropriate in the presence of a diluent, and also if appropriate in the presence of an acid binding agent, and if appropriate in the presence of a catalyst.

The malonic ester derivatives of the formula (XI) and also their salts and acid adducts are very highly suitable for the protection of plants against attack by undesirable microorganisms.

If 2,6-dichloro-isonicotinoyl chloride is used as the starting substance and dimethyl malonate as the reaction component, the course of process (e) can be illustrated by the following equation.

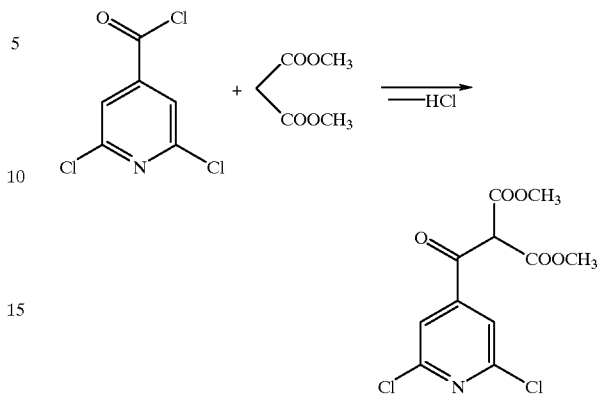

The malonic ester derivatives of the formula (XI) in general exist in the form of tautomer mixtures which can be characterized by the following formulae:

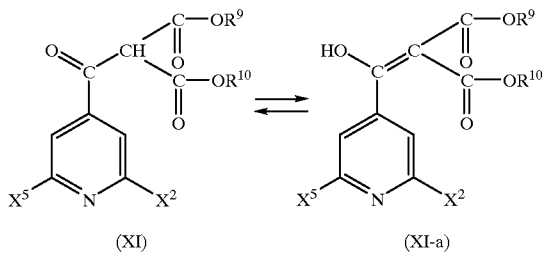

(XI)    (XI-a)

Formula (XIII) provides a general definition of the isonicotinoyl halides required as starting substances in carrying out process (e). In this formula $X^2$ and $X^5$ preferably have those meanings which have already been mentioned as preferred for these radicals in connection with the description of the compounds of the formula (IIa). $X^7$ preferably represents chlorine.

The isonicotinoyl halides of the formula (XIII) are known or can be prepared by processes which are known in principle (cf. J. Chem. Soc. 71 (1897), 1076).

Formula (XIVM provides a general definition of the malonic esters required as reaction components in carrying out process (e). In this formula $R^9$ and $R^{10}$ preferably have those meanings which have already been mentioned as preferred for these radicals in connection with the description of the malonic ester derivatives of the formula (XI).

The malonic esters of the formula (XIV) are known or can be prepared by known methods.

Diluents which can be employed in carrying out process (e) are all customary inert organic solvents. Those which can be preferably used are polar, aprotic solvents, such as ethers, such as dioxane, tetrahydrofuran or 1,2-dimethoxyethane, further amides, such as N,N-dimethylformamide, N,N-dimethylacetamide or N-methyl-pyrrolidone, furthermore nitriles, such as acetonitrile, propionitrile, n-butyronitrile or iso-butyronitrile, additionally sulphoxides, such as dimethyl sulphoxide, and also sulphones, such as sulpholane.

Acid-binding agents which can be employed in carrying out process (e) are all acid acceptors customary for reactions of this type. Those which can be preferably used are tertiary amines, such as trimethylamine, triethylamine, tributylamine, N,N-dimethylaniline, N,N-dimethylbenzylamine, pyridine, N-methylpyridine, N-methylmorpholine, N,N-dimethylaminopyridine, diazabicyclooctane (DABCO), diazabicyclononene (DBN) or diazabicycloundecene (DBU).

Suitable catalysts in carrying out process (e) are all reaction accelerators customary for reactions of this type. Those which can be preferably used are salts of polyvalent metals, such as magnesium chloride, zinc chloride, copper (I) sulphate or iron (III) chloride.

The reaction temperatures can be varied within a certain range in carrying out process (e). The reaction is in general carried out at temperatures between −20° C. and +40° C., preferably between −10° C. and +30° C.

Both process (e) and processes (c) and (d) are in general carried out under atmospheric pressure. However, it is also possible to carry out each of the processes under increased or reduced pressure.

In carrying out process (e), in general 0.5 to 2 mol, preferably 0.8 to 1.5 mol, of malonic ester of the formula (XIV) are employed per mole of isonicotinoyl halide of the formula (XII). Working up is carried out by customary methods. A procedure is in general used in which the reaction is acidified, the mixture obtained in this way is extracted with a poorly water-miscible organic solvent, and the combined organic phases are washed, optionally dried, and concentrated. The residual products can optionally be freed by customary methods from impurities which may possibly be present.

Possible diluents when carrying out process (d) are preferably water-miscible, organic solvents. Examples which may be mentioned are tetrahydrofuran, acetonitrite, dimethyl sulphoxide and sulpholane.

The reaction temperatures can be varied within a substantial range in carrying out process (d). The reaction is in general carried out at temperatures between 50° C. and 200° C., preferably between 80° C. and 180° C.

In carrying out process (d), in general 2 to 5 mol, preferably 2 to 2.5 mol, of water are employed per mole of malonic ester derivative of the formula (XI). Working up is carried out by customary methods. A procedure is in general used in which ice-water is added to the reaction, the resulting mixture is extracted several times with a poorly water-miscible organic solvent, the combined organic phases are washed with water in the presence of a base, then dried and concentrated, and the residue which remains is distilled.

Possible halogenating agents in carrying out process (c) are preferably bromine, chlorine, N-bromo-succinimide or N-iodo-succinimide.

Diluents which can be employed in carrying out process (c) are all customary inert, organic solvents. Those which can preferably be used are optionally halogenated aliphatic, alicyclic or aromatic hydrocarbons, such as hexane, cyclohexane, benzene, dichloromethane, chloroform, tetrachloromethane or trichloroethane.

Possible catalysts in carrying out process (c) are preferably Lewis acids, such as aluminium trichloride.

The reaction temperatures can also be varied within a substantial range in carrying out process (c). The reaction is in general carried out at temperatures between −20° C. and +120° C., preferably between 10° C. and 50° C.

In carrying out process (c), in general 0.5 to 5 mol, preferably 0.8 to 1.2 mol, of halogenating agent are employed per mole of acetylpyridine of the formula (X).

Working up is carried out by customary methods. A procedure is in general used in which water is added to the reaction mixture, the organic phase is washed successively with water in the presence of the base and then with water, subsequently dried and concentrated. The product obtained can be freed by customary methods from impurities which may possibly still be present.

Formula (III) provides a general definition of the thio compounds furthermore required as starting substances for carrying out process (a) according to the invention. In this formula (III), R preferably has those meanings which have already been mentioned as preferred for R in connection with the description of the compounds of the formula (I) according to the invention.

The thio compounds of the formula (III) are known synthesis chemicals.

The aminothiazoles of the formula (Ia) required as starting substances for carrying out process (b) according to the invention are substances according to the invention which can be prepared by process (a) according to the invention.

The formulae (IV) and (V) provide general definitions of the carboxylic anhydrides required as reaction components in carrying out process (b, variant α) according to the invention.

In these formulae, $R^5$ and A preferably have those meanings which have already been mentioned as preferred for these radicals in connection with the description of the pyridyl-thiazoles of the formula (I) according to the invention.

The carboxylic anhydrides of the formulae (IV) and (V) are known or can be prepared by known processes.

Formula (VI) provides a general definition of the carboxylic halides required as reaction components in carrying out process (b, variant β) according to the invention. In this formula, $R^5$ preferably has those meanings which have already been mentioned as preferred for this radical in connection with the description of the pyridyl-thiazoles according to the invention. $X^4$ preferably represents chlorine or bromine.

The carboxylic halides of the formula (VI) are known or can be prepared by known processes.

The formula (VII) provides a general definition of the isocyanates required as reaction components in carrying out process (b, variant γ) according to the invention. In this formula, $R^7$ preferably represents straight-chain or branched alkyl having 1 to 6 carbon atoms, aryl having 6 to 10 carbon atoms or arylsulphonyl having 6 to 10 carbon atoms, it being possible for each of the two latter radicals to be mono- to trisubstituted in the aryl part in an identical or different manner by halogen, cyano, nitro, formyl, carboxyl, carbamoyl, alkyl having 1 to 6 carbon atoms, alkoxy having 1 to 6 carbon atoms, alkylthio having 1 to 6 carbon atoms, alkylsulphinyl having 1 to 4 carbon atoms, alkylsulphonyl having 1 to 4 carbon atoms, halogenoalkyl having 1 to 4 carbon atoms and 1 to 5 fluorine, chlorine and/or bromine atoms, halogenoalkoxy having 1 to 4 carbon atoms and 1 to 5 fluorine, chlorine and/or bromine atoms, halogenoalkylthio having 1 to 4 carbon atoms and 1 to 5 fluorine, chlorine and/or bromine atoms, halogenoalkylsulphinyl having 1 to 4 carbon atoms and 1 to 5 fluorine, chlorine and/or bromine atoms, halogenoalkylsulphonyl having 1 to 4 carbon atoms and 1 to 5 fluorine, chlorine and/or bromine atoms, alkoxycarbonyl having 1 to 4 carbon atoms in the alkoxy part, hydroximinoalkyl having 1 to 4 carbon atoms in the alkyl part, alkoximinoalkyl having 1 to 4 carbon atoms in the alkoxy part and 1 to 4 carbon atoms in the alkyl part and/or divalent alkanediyl having 3 or 4 carbon atoms, in which one or two (non-adjacent) carbon atoms can be replaced by oxygen and in which the alkanediyl part can be mono- to tetrasubstituted in an identical or different manner by halogen, alkyl having 1 to 4 carbon atoms and/or halogenoalkyl having 1 or 2 carbon atoms and 1 to 3 fluorine, chlorine and/or bromine atoms.

$R^7$ particularly preferably represents methyl, ethyl, n-propyl, isopropyl, n-butyl, sec-butyl, iso-butyl, tert-butyl, phenyl, naphthyl, phenylsulphonyl or naphthylsulphonyl, it being possible for each of the four latter radicals to be mono- to trisubstituted in the aryl part in an identical or different manner by fluorine, chlorine, bromine, cyano, nitro, formyl, carboxyl, carbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methoxycarbonyl, hydroximinomethyl, hydroximinoethyl, methoximinomethyl, ethoximinomethyl, methoximinoethyl or ethoximinoethyl and/or in each case divalent trimethylene(propane-1,3-diyl), methylenedioxy or ethylenedioxy, which are in each case optionally mono- to tetrasubstituted in an identical or different manner by fluorine, chlorine, methyl, trifluoromethyl, ethyl or n- or i-propyl.

The isocyanates of the formula (VII) are known or can be prepared by known processes.

Formula (VIII) provides a general definition of the acetals required as reaction components in carrying out process (b), variant δ) according to the invention. In this formula, $R^3$ and $R^4$ preferably have those meanings which have already been mentioned as preferred for these radicals in connection with the description of the pyridyl-thiazoles of the formula (I) according to the invention. $R^8$ preferably represents methyl or ethyl.

Possible diluents in carrying out the process (a) according to the invention are all the customary inert organic solvents. Solvents which can preferably be used are aliphatic, alicyclic or aromatic hydrocarbons, such as, for example, petroleum ether, hexane, heptane, cyclohexane, methylcyclohexane, benzene, toluene, xylene or Decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; and sulphones such as sulpholane.

Possible acid-binding agents in carrying out process (a) according to the invention are all the customary inorganic or organic bases. Bases which can preferably be used are alkaline earth metal or alkali metal hydrides, hydroxides, amides, alcoholates, acetates, carbonates, or bicarbonates, such as, for example, sodium hydride, sodium amide, sodium methylate, sodium ethylate, potassium tertbutylate, sodium hydroxide, potassium hydroxide, sodium acetate, potassium acetate, calcium acetate, sodium carbonate, potassium carbonate, potassium bicarbonate or sodium bicarbonate, and furthermore ammonium compounds, such as ammonium hydroxide, ammonium acetate and ammonium carbonate, and in addition tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

However, it is also possible to carry out process (a) according to the invention in the absence of additional acid-binding agents.

The reaction temperatures can be varied within a substantial range in carrying out process (a) according to the invention. The reaction is in general carried out at temperatures between −20° C. and +100° C., preferably between 0° C. and 80° C.

Both process (a) according to the invention and process (b) are in general carried out under normal pressure. However, it is also possible to carry out each of the processes under increased or reduced pressure, for example between 0.1 bar and 10 bar.

In carrying out process (a) according to the invention, in general 0.8 to 10 mol, preferably 1 to 5 mol, of thio compound of the formula (III) are employed per mole of halogenoacetyl-pyridine of the formula (II). Working up is carried out by customary methods.

Possible diluents in carrying out process (b) according to the invention are all the customary inert organic solvents. Solvents which can preferably be used in the case of variants (α), (β) and (γ) are all those solvents which have already been mentioned as preferred in the case of process (a) according to the invention. Alcohols, such as methanol or ethanol, can also be employed as diluents for carrying out variant (δ).

Possible acid-binding agents for carrying out process (b), variants α and β, according to the invention are all the acid acceptors customary for such reactions. Acid acceptors which can preferably be used here are those acid-binding agents which have already been mentioned as preferred in the case of process (a) according to the invention.

Separate addition of a catalyst is in general unnecessary for carrying out variants (α) and (β) of process (b) according to the invention.

The addition of an acid-binding agent is in general not necessary for carrying out variants (γ) and (δ) of process (b) according to the invention.

Possible catalysts for carrying out variant (γ) of process (b) according to the invention are all the reaction accelerators customary for such reactions. Reaction accelerators which can preferably be used are amines, such as pyridine, dimethylaminopyridine and diazabicyclo-undecene (DBU).

Possible catalysts for carrying out variant (δ) of process (b) according to the invention are all the reaction accelerators customary for such reactions. Reaction accelerators which can preferably be used are acids, such as sulphuric acid, hydrochloric acid and toluenesulphonic acid, and furthermore also acid ion exchangers.

The reaction temperatures can also be varied within a substantial range when carrying out process (b) according to the invention. The reaction is in general carried out at temperatures between 0° C. and 150° C., preferably between 10° C. and 120° C.

In carrying out process (b) according to the invention, in general 0.8 to 15 mol. preferably 1 to 8 mol, of reaction component of the formula (IV), (V), (VI), (VII) or (VIII) are employed per mole of aminothiazole of the formula (Ia). Working up is carried out by customary methods.

For preparation of salts of compounds according to the invention, a procedure is in general followed in which a pyridyl-thiazole of the formula (Ib) is dissolved in an inert organic solvent, such as, for example, methanol or ethanol, and a strong base of the formula (IX) is added at room temperature or also at somewhat elevated temperature. Isolation and any purification required for the salts formed by this reaction are carried out by customary methods.

The pyridyl-thiazoles of the formula (I) according to the invention can also be converted into acid addition salts.

Possible acids for preparation of acid addition salts of the, compounds of the formula (I) are preferably those acids which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The active compounds according to the invention have a potent resistance-inducing action in plants. They are therefore suitable for generating resistance in plants against attack by undesirable microorganisms.

Resistance-inducing substances in the present connection are to be understood as those substances which are capable of stimulating the defence system of plants such that the treated plants, when subsequently inoculated with undesirable microorganisms, display substantial resistance to these microorganisms.

Undesirable microorganisms in the present case are to be understood as phytopathogenic fungi, bacteria and viruses. The substances according to the invention can thus be employed to generate resistance in plants against attack by the harmful organisms mentioned within a certain period of time after the treatment. The period of time within which resistance is brought about in general extends from 1 to 10 days, preferably 1 to 7 days, after treatment of the plants with the active compounds.

In addition to the resistance-inducing action, the active compounds according to the invention also have a potent microbicidal action and are also employed in practice for directly combating undesirable microorganisms. The active compounds are suitable for use as plant protection agents, in particular as fungicides.

Undesirable microorganisms in plant protection include fungi from the classes Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, and also treatment of vegetative propagation stock and seeds, and of the soil.

The active compounds according to the invention can also be used with particularly good success for combating cereal diseases, such as, for example, against Erysiphe species, or diseases in wine, fruit and vegetable growing, such as, for example, against Plasmopara or Venturia species, or rice diseases, such as, for example, against Pyricularia species. Other plant diseases, such as, for example, Septoria, Cochliobolus, Pyrenophora and Pseudocercosporella species, can also be combated with good success with the active compounds according to the invention.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can also be used as such or in their formulations as a mixture with known fungicides, bactericides, acaracides, nematicides or insecticides, in order thus, for example, to widen the action spectrum or prevent development of resistances.

Synergistic actions are observed in many cases in these mixtures.

Possible components for the mixtures are, for example:
Fungicides
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoximino-N-methyl-2-(2-phenoxy-phenyl)-acetamide; 8-hydroxyquinoline sulphate; methyl (E)-2-{2-[6-(2-cyano-phenoxy)-pyrimidine-4-yloxy]-phenyl}-3-methoxyacrylate; methyl (E)-methox-imino[alpha-(o-tolyloxy)o-tolyl]acetate; 2-phenylphenol (OPP), aldimorph, ampropylfos, anilazine, azaconazole,
benalaxyl, benodanil, benomyl, binapacryl, biphenyl, bitertanol, blasticidin-S, bromuconazole, bupirimate, buthiobate,
calcium polysulphide, captafol, captan, carbendazim, carboxin, chinomethionat (quinomethionate), chloroneb, chloropicrin, chlorothalonil, chlozolinat, cufraneb,
cymoxanil, cyproconazole, cyprofuram,
dichlorophene, dichlobutrazole, diclofluanid, diclomezin, dichloran, diethofencarb,
difenoconazole, dimethirimol, dimethomorph, diniconazole, dinocap, diphenylamine, dipyrithione, ditalimfos, dithianon, dodine, drazoxolon,
edifenphos, epoxyconazole, ethirimol, etridiazole,
fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutoanil, flutriafol, folpet, fosetyl-aluminium, fthalide, fuberidazole, furalaxyl, furmecyclox,
guazatine,
hexachlorobenzene, hexaconazole, hymexazole,
imazalil, imibenconazole, iminoactadin, iprobenfos (IBF), iprodione, isoprothiolan,
kasugamycin, copper formulations, such as: copper hydroxide, copper naphthenate, copper oxychloride, copper sulphate, copper oxide, oxine-copper and Bordeaux mixture,
mancopper, mancozeb, mepanipyrim, mepronil, metalaxyl, metconazole,
methasulphocarb, methfuroxam, metiram, metsulphovax, myclobutanil,
nickel dimethyldithiocarbamate, nitrothal-isopropyl, nuarimol,
ofurace, oxadixyl, oxamocarb, oxycarboxin,
perfurazoat, penconazole, pencycuron, phosdiphen, pimaricin, piperalin, polyoxin, probenazole, prochloraz, procymidon, propamocarb, propiconazole, propineb, pyrazophos, pyrifenox, pyrimethanil, pyroquilone
quintozene (PCNB),
sulphur and sulphur formulations,
tebuconazole, tecloftalam, tecnazene, tetraconazole, thiabendazole, thicyofen, thiophanate-methyl, thiram, tolclophos-methyl, tolylfluanid, triadimefon, triadimenol, triazoxid, trichlamid, tricyclazole, tridemorph, triflumizole, triforine, triticonazole,
validamycin A, vinclozolin,
zineb, ziram
Bactericides
bronopol, dichlorophen, nitrapyrin, nickel dimethyldithiocarbamate, kasugamycin, octhilinon, furancarboxylic acid, oxytetracycline, probenazole, streptomycin, tecloftalam, copper sulphate and other copper formulations.
Insecticides/Acaricides/Nematicides
abamectin, AC 303 630, acephate, acrinathrin, alanycarb, aldicarb, alphamethrin, amitraz, avermectin AZ 60541, azadirachtin, azinphos A, azinphos M, azocyclotin,
Bacillus thuringiensis, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin,
clocythrin, clofentezin, cyanophos, cycloprothin, cyfluthrin, cyhalothrin, cyhexatin, cypermethrin, cyromazin,
deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb,
fenoxycarb, fenpropathrin, fenpyrad, fenpyroximate, fenthion, fenvalerate,
fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulphenphos, metaldehyde, methacrifos,
methamidophos, methidathion, methiocarb, methomyl, metolcarb, milbermectin,
monocrotophos, moxidectin,
naled, NC 184, NI 25, nitenpyram
omethoate, oxamyl, oxydemethon M, oxydeprofos,
parathion A, parathion M, pennethrin, phenthoate, phorate, phosalone, phosmet,
phosphamidon, phoxim, pirimicarb, pirimiphos M, pirimiphos A,
profenophos, promecarb, propaphos, propoxur, prothiofos, prothiophos, prothoate,
pymetrozin, pyrachlophos, pyridaphenthion, pyresmethrin, pyrethrum, pyridaben, pyrimidifen pyriproxifen,
quinalphos,
RH 5992,
salithion, sebufos, silafluofen, sulphotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

The active compounds according to the invention can also be mixed with other known active compounds, such as herbicides, or also with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range: they are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of active compounds according to the invention are illustrated by the following examples.

PREPARATION EXAMPLES

Example 1

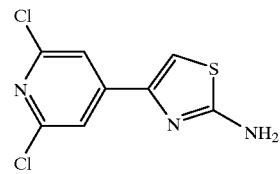

931.5 g (3.46 mol) of 4-bromoacetyl-2,6-dichloropyridine and 318.2 g (4.18 mol) of thiourea are brought together in 4.2 litres of acetone, stirring, during which the temperature rises to 45° C. The mixture is stirred for a further 3 hours. The solid obtained by this procedure is filtered off with suction, washed with a little acetone and dried while further filtering with suction. The product thus obtained is suspended in 2 liters of water at room temperature, a pH of 10 is established by addition of concentrated aqueous sodium hydroxide solution, and the solid is filtered off with suction again, rinsed with 3 liters of water and dried at 50° C. under reduced pressure. The crude product thus obtained is stirred with 30 litres of tert-amyl methyl ether and the mixture obtained by this procedure is filtered with suction. The filtrate is concentrated under reduced pressure and the residue which remains is dried at 50° C. under reduced pressure. The solid isolated after the tert-amyl methyl ether mixture has been filtered with suction is dissolved in 1 liter of hot ethanol. The solution formed is filtered and the filtrate is then cooled to 5° C. The solid which precipitates in this procedure is also filtered off with suction and dried at 50° C. under reduced pressure. A total of 600.1 g (70.5% of theory) of [4-(2,6-dichloropyridin-4-yl)-thiazol-2-yl]-amine are obtained in this manner as a solid substance of melting point 239 to 247° C.

Preparation of Starting Substances

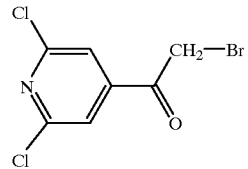

(II-1)

First 2 g of aluminium chloride are added to a solution of 525 g (2.763 mol) of 4-acetyl-2,6-dichloro-pyridine in 1.37 liters of dichloromethane and then 417.6 g (2.613 mol) of bromine are added dropwise with stirring at 30 to 35° C. in the course of 30 minutes. After addition is complete, the reaction mixture is subsequently stirred for a further hour at 35° C. and 1.2 l of water are then added. The organic phase is separated off and washed successively, first with 1.2 l of saturated, aqueous sodium hydrogen carbonate solution and then twice with 1.2 l of water each time. It is dried over sodium sulphate and then concentrated under reduced pressure. The residue which remains is stirred with 2 l of petroleum ether, then filtered off with suction and washed in portions with a total of 1 liter of petroleum ether. The product obtained is dried at 50° C. under reduced pressure. In this manner 592.2 g (79.7% of theory) of 4-bromo-acetyl-2,6-dichloro-pyridine are obtained in the form of a solid substance.

$^1$H-NMR spectrum (CDCl$_3$/TMS): δ=4.42 (s, 2H); 7.74 (s, 2H) ppm

23

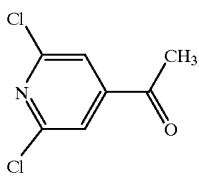

(X-1)

1328 g (4.34 mol) of dimethyl 2,6-dichloro-isonicotinoyl-malonate are dissolved in a mixture of 3.45 l of dimethyl sulphoxide and 156.2 g (8.68 mol) of water. The reaction mixture is heated to 140° C. and stirred at this temperature for 30 minutes. After this, the reaction mixture is cooled to 10° C. and then added to 8.4 l of ice-water. The mixture is extracted twice with a total of 3.6 l of dichloromethane and the combined organic phases are washed once with 1.5 l of saturated, aqueous sodium hydrogen carbonate solution. After drying over sodium sulphate, the organic phase is concentrated under reduced pressure. The residue which remains is distilled under reduced pressure. In this manner 506.0 g (60% of theory) of 4-acetyl-2,6-dichloropyridine of boiling point 98° C. at 0.5 mbar are obtained.

(XI-1)

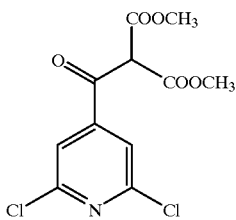

2312 g (24.28 mol) of magnesium chloride are introduced with cooling into 18 l of acetonitrile. After the exothermic reaction has subsided, the solution is cooled to 0° C. and 3210 g (24.3 mol) of dimethyl malonate are added dropwise with stirring in the course of 45 minutes. After this, 4920 g (48.62 mol) of triethylamine are added dropwise at 0° C. with stirring in the course of 1.5 hours. After addition is complete, the mixture is stirred at 0° C. for a further 15 minutes. A solution of 4742 g (22.53 mol) of 2,6-dichloro-isonicotinyl chloride in 6670 ml of acetonitrile is then added dropwise at 0° C. with stirring in the course of 20 hours. The mixture is first stirred for 1 hour at 0° C. and then for 16 hours while slowly warming to room temperature. 15.9 l of concentrated hydrochloric acid are then added dropwise with stirring to the reaction mixture with cooling to 0 to 10° C. After this, 15.9 l of dichloromethane and 6.4 l of water are added with stirring and the organic phase is then separated off. The aqueous phase is extracted once more with 7.9 l of dichloromethane. The combined organic phases are washed twice with 4 l of water each time and then concentrated under reduced pressure. The residue which remains is stirred with 9.5 l of water, then filtered off with suction and washed successively, first with 6.3 l of water and then twice with 7.9 l of petroleum ether each time. The product obtained is dried at 40° C. under reduced pressure. In this manner, 6.17 kg (89.2% of theory) of dimethyl 2,6-dichloro-isonicotinoyl-malonate are obtained.

$^1$H-NMR spectrum (CDCl$_3$/TMS): δ=3.68; 3.84; 3.92 and 7.39 ppm.

24

Example 2

7.53 g (0.03 mol) of 2-trifluoromethylphenylsulphonyl isocyanate are added to a solution of 7.38 g (0.03 mol) of [4-(2,6-dichloropyridin-4-yl)-thiazol-2-yl]-amine in 180 ml of acetonitrile at 75° C. in the course of 5 minutes, while stirring. The reaction mixture is stirred at 75° C. for a further 3 hours and then cooled to room temperature, and the solid which has precipitated out is filtered off with suction, washed twice with 10 ml of acetonitrile each time and dried at 45° C. under reduced pressure. 14 g (93.9% of theory) of N-[4-(2,6-dichloro-pyridin-4-yl)-thiazol-2-yl]-N'-(2-trifluoromethyl-phenylsulphonyl)-urea are obtained in this manner in the form of a solid substance with a melting point of >280° C.

Example 3

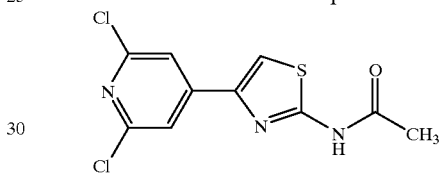

7.38 g (0.03 mol) of [4-(2,6-dichloropyridin-4-yl)-thiazol-2-yl]-amine and 70 ml of acetic anhydride are heated under reflux for 30 minutes, a solution initially forming but a precipitate then separating out. The reaction mixture is left to stand at room temperature for 16 hours, 200 ml of ice-water are then added and the mixture is filtered with suction. The residue is first washed several times with water and then digested with 200 ml of 5% strength aqueous sodium bicarbonate solution, and is filtered off with suction again. The product is dried at 50° C. under reduced pressure. 8.1 g (93.8% of theory) of N-[4-(2,6-dichloropyridin-4-yl)-thiazol-2-yl]-acetamide are obtained in this manner in the form of a solid substance of melting point 301° C.

Example 4

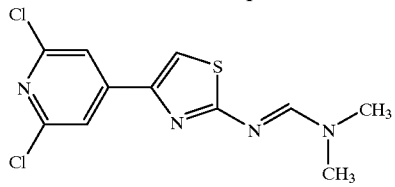

3.93 g (0.033 mol) of dimethylformamide dimethyl acetal are added to a mixture of 7.38 g (0.03 mol) of [4-(2,6-dichloropyridin-4-yl)-thiazol-2-yl]-amine and 50 ml of methanol at 20° C., while stirring, and the mixture is stirred at 50° C. for a further 2 hours. Thereafter, the reaction mixture is cooled to 10° C. and filtered with suction. The residue is washed with 10 ml of cold methanol and then dried at 45° C. under reduced pressure. 7.5 g (83% of theory) of N-[4-(2,6-dichloropyridin-4-yl)-thiazol-2-yl]-N,N'-dimethylformamidine are obtained in this manner in the form of a solid substance of melting point 145° C.

The compounds of the formula

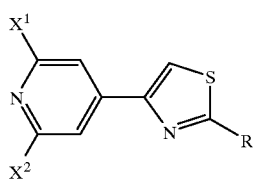

(I)

listed in the following table are also prepared by the methods described above.

TABLE 1

| Ex. No. | X¹ | X² | R | Melting point (° C.) |
|---|---|---|---|---|
| 5 | Cl | Cl | —CH₃ | 131–133 |
| 6 | Cl | Cl | (N-pyrroledione with two CH₃ groups) | 278 |
| 7 | Cl | Cl | —NH—C(O)—N⁻(Na⁺)—SO₂—C₆H₄—CF₃ | 300 (decomposition) |
| 8 | Cl | Cl | —NH—C(=O)—C₆H₃(OCH₃)₂ | 168 (decomposition) |

TABLE 1-continued

| Ex. No. | X¹ | X² | R | Melting point (° C.) |
|---|---|---|---|---|
| 9 | Cl | Cl | —NH—CO—CO—OC₂H₅ | 163 |

Use Examples

Example A

Plasmopara Test (Vines)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous spore suspension of *Plasmopara viticola* and then remain in a humidity chamber at 20 to 22° C. and 100% relative atmospheric humidity for 1 day. The plants are then placed in a greenhouse at 21° C. and about 90% atmospheric humidity for 5 days. The plants are then moistened and placed in a humidity chamber for 1 day.

Evaluation is carried out 6 days after the inoculation. In this evaluation, 0% denotes a degree of action which corresponds to that of the control, while a degree of action of 100% denotes that no attack is observed.

The active compounds, active compound concentrations and test results can be seen from the following table.

TABLE A

Plasmopara test (vines)/protective

| Active compound | Degree of action in %, based on the untreated control, at an active compound concentration in the spray liquor of 100 ppm |
|---|---|

According to the invention:

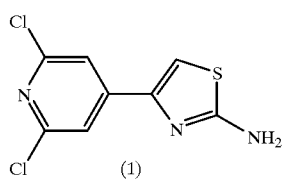

(1)

81

TABLE A-continued

Plasmopara test (vines)/protective

| Active compound | Degree of action in %, based on the untreated control, at an active compound concentration in the spray liquor of 100 ppm |
|---|---|
| 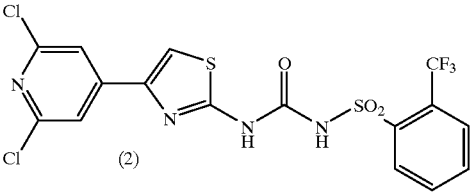 (2) | 85 |

Example B
Venturia Test (Apple)/Protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism *Venturia inaequalis* and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation. In this evaluation, 0% denotes a degree of action which corresponds to that of the control, while a degree of action of 100% denotes that no attack is observed.

The active compound, active compound concentrations and test results can be seen from the following table.

TABLE B

Venturia test (apple)/protective

| Active compound | Degree of action in %, based on the untreated control, at an active compound concentration in the spray liquor of 10 ppm |
|---|---|
| According to the invention: | |
| 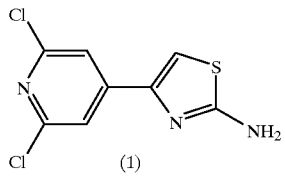 (1) | 76 |
| 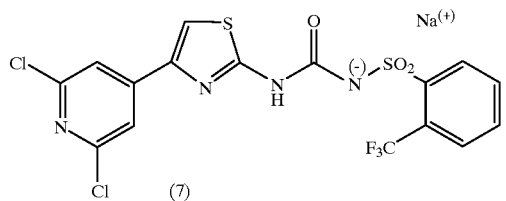 (7) | 66 |

TABLE B-continued

Venturia test (apple)/protective

| Active compound | Degree of action in %, based on the untreated control, at an active compound concentration in the spray liquor of 10 ppm |
|---|---|
| Compound (8): 2,6-dichloropyridin-4-yl thiazole with NH-C(=O)-(2,6-dimethoxyphenyl) substituent | 72 |

Example C
Erysiphe Test (Barley)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation. In this, 0% denotes a degree of action which corresponds to that of the control, while a degree of action of 100% denotes that no attack is observed.

The active compounds, active compound concentrations and test results can be seen from the following table.

TABLE C

Erysiphe test (barley)/protective

| Active compound | Degree of action in %, based on the untreated control, at an amount of active compound applied of 250 g/ha |
|---|---|
| According to the invention: | |
| Compound (1): 2,6-dichloropyridin-4-yl thiazol-2-amine | 77 |

Example D
Erysiphe Test (Barley)/Curative

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f. sp. *hordei*. 48 hours after the inoculation, the plants are sprayed with the preparation of active compound in the stated amount applied.

The plants are placed in a greenhouse at a temperature of about 20° C. and a relative atmospheric humidity of about 80%, in order to promote the development of powdery mildew pustules.

Evaluation is carried out 7 days after the inoculation. In this evaluation, 0% denotes a degree of action which corresponds to that of the control, while a degree of action of 100% denotes that no attack is observed.

The active compounds, active compound concentrations and test results can be seen from the following table.

TABLE D

Erysiphe test (barley)/curative

| Active compound | Degree of action in %, based on the untreated control, at an amount of active compound applied of 250 g/ha |
|---|---|
| According to the invention: | |
| Compound (1): 2,6-dichloropyridin-4-yl thiazol-2-amine | 75 |

Example E
Pyricularia Test (Rice)/Protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. 4 days after the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation. In this evaluation, 0% denotes a degree of action which corresponds to that of the control, while a degree of action of 100% denotes that no attack is observed.

The active compounds, active compound concentrations and test results can be seen from the following table.

TABLE E

Pyricularia test (rice)/protective

| Active compound | Active compound concentration in the spray liquor in % by weight | Degree of action in %, based on the untreated control |
|---|---|---|
| According to the invention: | | |
| 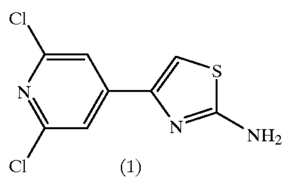  (1) | 0,025 | 90 |

Example F

Pyricularia Test (Rice)/Systemic

Solvent: 12.5 parts by weight of acetone

Emulsifier: 0.3 parts by weight of alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for systemic properties, 40 ml of the preparation of active compound are poured onto standard soil, in which young rice plants have been grown. 7 days after the treatment, the plants are inoculated with an aqueous spore suspension of *Pyricularia oryzae*. The plants then remain in a greenhouse at 100% relative atmospheric humidity and 25° C. until evaluation.

Evaluation of the disease infestation is carried out 4 days after the inoculation. In this, 0% denotes a degree of action which corresponds to that of the control, while a degree of action of 100% denotes that no attack is observed.

The active compounds, active compound concentrations and test results can be seen from the following table.

TABLE F

Pyricularia test(rice)/systemic

| Active compound | Amount applied in mg of active compound per 100 $cm^2$ | Degree of action in %, based on the untreated control |
|---|---|---|
| According to the invention: | | |
| 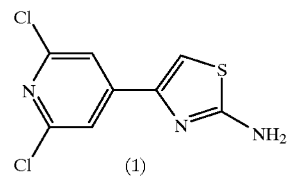  (1) | 100 | 80 |

What is claimed is:

1. A halogenoacetyl-pyridine of the formula 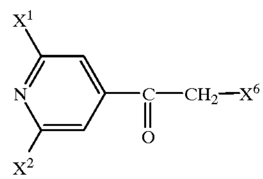 (IIa)

in which $X^2$ represents chlorine, $X^5$ represents chlorine and $X^6$ represents chlorine or bromine.

2. A process for the preparation of a halogenoacetyl-pyridine according to claim 1, which process comprises reacting an acetylpyridine of the formula 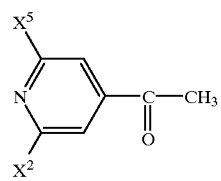 (X)

in which $X^2$ and $X^5$ have the above-mentioned meanings, with bromine, chlorine or N-bromo succinimide in the presence of a diluent.

* * * * *

UNITED STATES PATENT AND TRADEMARK OFFICE
CERTIFICATE OF CORRECTION

PATENT NO. : 6,160,121 Page 1 of 1
DATED : December 12, 2000
INVENTOR(S) : Gallenkamp et al.

It is certified that error appears in the above-identified patent and that said Letters Patent is hereby corrected as shown below:

<u>Column 32,</u>
Line 25, delete " 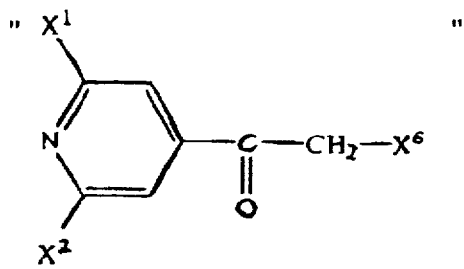 "

and substitute -- 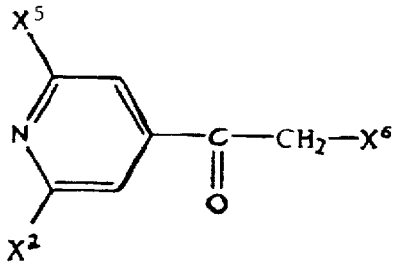 --

Signed and Sealed this

Twelfth Day of March, 2002

Attest:

JAMES E. ROGAN
*Attesting Officer*    *Director of the United States Patent and Trademark Office*